United States Patent
Zhang et al.

(10) Patent No.: US 10,246,401 B2
(45) Date of Patent: *Apr. 2, 2019

(54) CRYSTALLINE FORM OF CHLOROGENIC ACID AND PREPARATION METHOD THEREOF

(71) Applicant: SICHUAN JIUZHANG BIOLOGICAL SCIENCE AND TECHNOLOGY CO., LTD., Chengdu, Sichuan (CN)

(72) Inventors: Jie Zhang, Sichuan (CN); Liang Zhang, Sichuan (CN); Wang Huang, Sichuan (CN)

(73) Assignee: SICHUAN JIUZHANG BIOLOGICAL SCIENCE AND TECHNOLOGY CO., LTD., Chengdu, Sichuan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/308,034

(22) PCT Filed: May 16, 2014

(86) PCT No.: PCT/CN2014/077652
§ 371 (c)(1),
(2) Date: Oct. 31, 2016

(87) PCT Pub. No.: WO2015/168963
PCT Pub. Date: Nov. 12, 2015

(65) Prior Publication Data
US 2017/0050915 A1 Feb. 23, 2017

(30) Foreign Application Priority Data
May 9, 2014 (CN) .......................... 2014 1 0193699

(51) Int. Cl.
*C07C 67/52* (2006.01)
*C07C 69/618* (2006.01)
*C07C 69/732* (2006.01)

(52) U.S. Cl.
CPC ............ *C07C 69/618* (2013.01); *C07C 67/52* (2013.01); *C07C 69/732* (2013.01); *C07B 2200/13* (2013.01); *C07C 2601/14* (2017.05)

(58) Field of Classification Search
None
See application file for complete search history.

(56) References Cited

U.S. PATENT DOCUMENTS 3,328,170 A * 6/1967 Hamamura ............ A23K 50/90
119/270
4,872,987 A * 10/1989 Kopsch .................... A23F 5/02
210/635
2017/0319530 A1* 11/2017 Zhang .................. A61K 31/216

FOREIGN PATENT DOCUMENTS

CN 101343225 * 1/2009
CN 101486651 * 7/2009

(Continued)

OTHER PUBLICATIONS

Wu, Lingling et al., "Crystal Structural Determination of Chlorogenic Acid by X-Ray Powder Diffraction", Chinese Journal of Experimental Traditional Medical Formulae, vol. 16, No. 17, Dec. 31, 2010.

(Continued)

*Primary Examiner* — Amy C Bonaparte
(74) *Attorney, Agent, or Firm* — Novick, Kim & Lee, PLLC; Allen Xue

(57) ABSTRACT

Provided is a crystalline form of chlorogenic acid. The crystalline form is an orthorhombic crystal system, the space group is $P2_12_12_1$, the cell parameters are a=7.7291 (2) Å, b=10.9808 (2) Å, and c=3.5334 (7) Å, $\alpha=\beta=\gamma=90.00°$, Z=8, and the cell volume is 3100.65 (11) Å$^3$. Also provided is a preparation method for the crystalline form. The present crystalline form has good stability and does not significantly (Continued)

change during storage for 48 months in a cool, dark place, and the various indices all meet the relevant requirements for active pharmaceutical ingredients. The crystallization process provided by the present invention can not only use raw materials having different purities to prepare the same crystalline form of chlorogenic acid, but can also significantly reduce solvent residue in the raw materials, thereby improving product safety.

16 Claims, 2 Drawing Sheets

(56) References Cited

FOREIGN PATENT DOCUMENTS

| CN | 101602668 | * | 12/2009 |
|----|-----------|---|---------|
| CN | 101805261 | * | 8/2010 |
| CN | 102391117 | * | 3/2012 |
| CN | 102476997 A | | 5/2012 |
| CN | 102746153 | * | 10/2012 |
| CN | 102755366 | * | 10/2012 |
| CN | 102786417 | * | 11/2012 |
| CN | 102786418 A | | 11/2012 |
| CN | 101851163 | * | 12/2012 |
| CN | 103012518 | * | 4/2013 |
| CN | 103420838 | * | 12/2013 |
| CN | 103450019 | * | 12/2013 |

OTHER PUBLICATIONS

Yang Lu, Polymorphic Drugs, People's Medical Publishing House, 2009, 1st edition, ISBN: 9787117115711, p. 24-25.

* cited by examiner

CRYSTALLINE FORM OF CHLOROGENIC ACID AND PREPARATION METHOD THEREOF

TECHNICAL FIELD

The present invention relates to a new crystal form of chlorogenic acid.

BACKGROUND ART

Chlorogenic acid, also named as 3-O-caffeoylquinnic acid, is a kind of polyphenol compound which exists widely in plants, whose content is higher in the plants *Lonicera japonica* Thunb., *Eucommia ulmoides* Oliv., coffee and so on. Chlorogenic acid possesses better activities of antiallergic reactions, regulating blood sugar, scavenging oxygen radicals, anticancer, and anti-HIV. Extensive research focuses on it due to its evident effects, as well as insignificant toxicity and side effects.

For one compound, there may be two or more different crystalline states, while different crystal form may generally exhibit different bioavailability, dissolution, solubility rate, stability, melting point, color, filterability, density, and fluidity. Therefore, as for drugs, it has very important significance to prepare the crystal forms with better solubility and stability.

Lingling Wu et al used chlorogenic acid, purchased from National Institute for the Control of Pharmaceutical and Biological Products of China, as starting materials, and made a study on the crystal structures. They found that the control chlorogenic acid with batch number 110753 belonged to orthorhombic system and space group Pna21, with unit cell parameters a=36.132 Å, b=11.709 Å, c=8.152 Å, $\alpha=\beta=\gamma=90°$, number of molecules in the unit cell (Z)=4, unit cell volume=3448.86 $Å^3$ (Lingling Wu, et al, Crystal structure analysis of chlorogenic acid by X-ray powder diffraction [J]. Chinese Journal of Experimental Traditional Medical Formulae, 2010, 16(17)). This literature didn't further show the beneficial effects and preparation method of the crystal form.

CONTENTS OF THE INVENTION

One object of the present invention is to provide a crystal form of chlorogenic acid. Another object of the present invention is to provide the method for preparation of the crystal form. The present invention provides a crystal form of chlorogenic acid, which belongs to orthorhombic system, with space group $P2_12_12_1$ and cell parameters: a=7.7291(2) Å, b=10.9808(2) Å, c=36.5334(7) Å, $\alpha=\beta=\gamma=90°$, Z=8, unit cell volume=3100.65(11) $Å^3$.

More further, X-ray powder diffraction spectrum of said crystal form is shown in FIG. 1 or FIG. 2.

Currently, there have not been methods related with preparation of said crystal form. Thus, the present invention also provides the preparation process of said crystal form, that includes one of the following methods:

Method 1: Taking chlorogenic acid with a purity of more than 98%, dissolving it in water, filtering, freeze-drying the filtrate, to obtain the crystal form of chlorogenic acid;

Method 2: Taking chlorogenic acid with a purity of more than 90%, dissolving it in water, filtering for the first time, freezing the filtrate to 5° C.--20° C. at the ambient temperature of below 0° C., filtering for the second time, freeze-drying the filter residue, to obtain the crystal form of chlorogenic acid.

The purity of chlorogenic acid raw material in Method 2 is more than 90%. It includes chlorogenic acid raw material of Method 1, with purity of above 98%, which means, the crystal form according to the present invention can also be prepared by Method 2 using chlorogenic acid with purity of more than 98%. Chlorogenic acid raw material used in the present invention can be obtained by commercially available product, and can also be obtained by purification according to the prior art, as long as it ensures that the purity of chlorogenic acid is within the scope of the present invention.

The process of "Freezing the filtrate to 5° C.--20° C. at the ambient temperature of below 0° C." can use the freezing function of a refrigerator, or use other ways, such as ice-water bath, liquid nitrogen, etc.

More further, in method 1 or 2, the temperature of dissolving chlorogenic acid in water is at 5° C.-70° C.

More further, in method 1, chlorogenic acid is dissolved in water with the concentration of 10 mg/ml-2 g/ml; in method 2, chlorogenic acid is dissolved in water with the concentration of 20 mg/ml-2 g/ml.

Further, in method 1 or 2, the aperture size of the filter used for filtration is 0.22 μm-200 μm.

The filter used in the present invention means the tool used for filtering liquid. It is a porous article or substance (e.g. cloth, paper, membrane, etc.), and works as a medium used to separate suspended materials or dissolved impurities or pigments, etc., from liquid flowing through it. The forms of filter can be common filter membranes or filter elements, but not limit to two said kinds.

Further, in method 1, the filter used for filtration is filter membranes or filter elements; in method 2, the filter used for the first filtration is filter membranes or filter elements are, while the filter used for the second filtration is filter membranes.

Further, in method 1, the filtration temperature is at 5° C.-70° C.; in method 2, the temperature of first filtration is at 5° C.-70° C., while the temperature of second filtration is at 0° C.-25° C.

Further, in method 1, the conditions for freeze-drying are as follows: the pre-freezing temperature is -20° C.--50° C.; the pre-freezing time is 1 h-8 h; the drying temperature is from -20° C.--50° C. to 30° C.; the warming time is 8 h-48 h; drying at 30° C. for another 1 h-12 h; the vacuum degree is 5 Pa-40 Pa during freeze-drying.

In Method 2, the conditions for freeze-drying are as follows: the pre-freezing temperature is -10° C.--30° C., the pre-freezing time is 1 h-5 h; the drying temperature is from -10° C.--30° C. to 30° C.; the warming time is 8 h-48 h; drying for another 1 h-12 h at 30° C.; the vacuum degree is 5 Pa-40 Pa during freeze-drying.

It is well known that a same chemical drug produces different crystal solids with varied temperature parameters of crystallization under the same conditions of recrystallization solvent; the same chemical drug may possibly produce different crystal forms under different conditions of recrystallization solvents, due to the parameter change including the types and amounts of crystallization solvent contained in the crystals, the amounts and position of crystallization water contained in the crystals, as well as the chirality and the conformation of drug molecules contained in the crystals (Polymorphic Drugs, Yang Lv, People's Medical Publishing House, 2009, 1st edition, pages 24-25). Thus, it can be seen that the structure of the crystal form prepared with different crystallization methods or parameters is unpredictable, even with the same raw material.

As for the present invention, the purity of the raw material used in methods 1 and 2 might be different, and the conditions of filtering, freeze-drying, etc. are also different. Therefore, in the absence of corresponding data comparison, it is also unpredictable whether the structures of the crystal forms prepared by two methods are same. The present invention compares the crystal forms prepared by two methods via X-ray powder diffraction data. Surprisingly, it is found that both structures obtained by two methods are same and belong to the same crystal form.

In addition, during the process of preparing crystal forms by method 2, surprisingly, it is found that the purity of chlorogenic acid product could be effectively increased by the second filtration after freezing the filtrate of the first filtration at 5° C.--20° C., and it can purify the chlorogenic acid crude material with a purity of more than 90% and less than 98%, to obtain pure product with a purity as high as 98% or more. Thus, the present invention also provides the method for purifying chlorogenic acid, which includes the following steps:

Taking crude chlorogenic acid with a purity of more than 90% and less than 98%, dissolving chlorogenic acid in water, filtering for the first time, freezing the filtrate to 5° C.--20° C. at the ambient temperature of below 0° C., filtering for the second time, freeze-drying the filter residue, to obtain chlorogenic acid pure product with a purity of more than 98%.

Further, the temperature of dissolving chlorogenic acid in water is at 5° C.-70° C.

Further, chlorogenic acid is dissolved in water with the concentration of 20 mg/ml-2 g/ml.

Further, the aperture size of the filter used for filtration is 0.22 μm-200 μm.

Further, the filter used for first filtration is a filter membrane or a filter element, while the filter used for second filtration is a filter membrane.

Further, the temperature of first filtration is at 5° C.-70° C., while the temperature of second filtration is at 0° C.-25° C.

Further, the conditions for freeze-drying are as follows: the pre-freezing temperature is −10° C.--30° C.; the pre-freezing time is 1 h-5 h; the drying temperature is from −10° C.--30° C. to 30° C.; the warming time is 8 h-48 h; drying at 30° C. for another 1 h-12 h; the vacuum degree is 5 Pa-40 Pa during freeze-drying.

The advantages of the present invention are:
(1) The stability of the chlorogenic acid crystal form provided by the present invention is good. It does not change obviously within 48 months when stored in the cool and dark place, and all indicators accord with relevant requirements of crude drugs;
(2) The crystallization process provided by the present invention can not only prepare the same chlorogenic acid crystals from raw materials with different purities, but also significantly reduce the solvent residues in the raw materials and improve the safety of the product.
(3) In the process of preparing the crystal form by method 2, it is surprisingly found that the purity of chlorogenic acid product could be effectively increased by the second filtration after freezing the filtrate of the first filtration at 5° C.--20° C., and it can purify the chlorogenic acid crude material with a purity of more than 90% and less than 98%, to obtain pure product with a purity as high as 98% or more. Additionally, while filtering for the second time, a large amount of water is removed effectively by separating the filter residue from the filtrate. While in later stage, the drying time of freeze-drying can be shorter than that of method 1, and the drying cost can also be lower. Meanwhile, method 2 can use raw material with lower purity, and have a wider applicability. Thus, the present invention can further prefer method 2 as preparation method of the chlorogenic acid crystal form.
(4) The purification method of chlorogenic acid provided by the present invention can significantly improve the purity of chlorogenic acid to be more than 98%, by freezing, filtering and other operations, providing new choices for preparing chlorogenic acid with high purity.

The following examples are provided to further illustrate the present invention, but it does not limit the present invention. All modifications and substitutions made according to the present invention by those skilled in the art should belong to the scope of the claims of the present invention, as long as they do not depart from the spirit of the present invention.

EXAMPLES

Example 1 Preparation Method of Chlorogenic Acid Crystal Forms According to the Present Invention Processes: preparing solution-filtering-freeze-drying (1) Preparing solution: Taking chlorogenic acid with a purity of more than 98%, adding purified water or water for injection, to prepare the solution chlorogenic acid with a concentration of 10 mg/ml-2 g/ml, and the dissolution temperature is 5° C.-70° C.;
(2) Filtering: the prepared aqueous solution of chlorogenic acid is filtered by a filter membrane or a filter element with an aperture size of 0.22 μm-200 μm, and the filtration temperature is 5° C.-70° C. The filtrate is collected; (3) Freeze-drying: The filtrate is placed in lyophilizer to freeze-dry, using a pre-freezing temperature of −20° C.--50° C., pre-freezing time of 1 h-8 h, a vacuum degree of 5 Pa-40 Pa, a drying temperature of from −20° C.--50° C. to 30° C., a warming time of 8 h-48 h, and drying for another 1 h-12 h at 30° C. After freeze-drying, the chlorogenic acid crystal form according to the present invention is obtained.

The crystal form prepared according to Example 1 is detected, and the relevant data are shown in Table 1:
1. Single Crystal X-Ray Diffraction

| | |
|---|---|
| syngony | Orthorhombic system |
| space group | P212121 |
| a/Å | 7.7291(2) |
| b/Å | 10.9808(2) |
| c/Å | 36.5334(7) |
| α/° | 90 |
| β/° | 90 |
| γ/° | 90 |
| volume/Å³ | 3100.65(11) |
| number of units in the unit cell (Z) | 8 |
| F(000) | 1528 |

2. Powder X-Ray Diffraction
Instrument model: Philips MRD X-ray diffractometer (Britain) Detection criterion: Powder diffraction data issued by International Center for Diffraction Data (ICDD)

Figure 1:
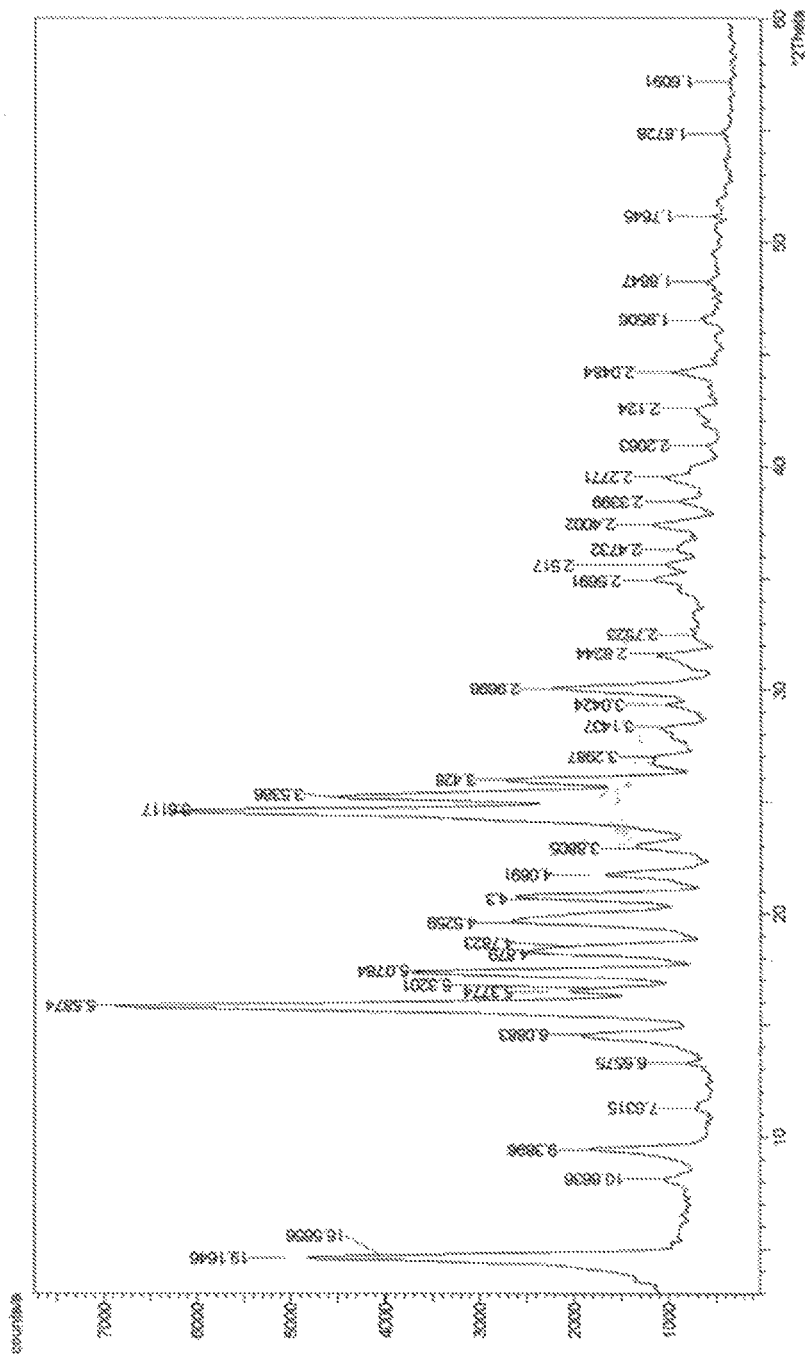
FIG. 1: X-ray powder diffraction spectrum of the chlorogenic acid crystal form prepared by Example 1

Testing conditions: target material Cu/graphite; tube voltage: 40 KV;
tube current: 30 mA; range 0.00-60.00 (Deg); scanning speed: 2 Deg/min
Testing results are shown in FIG. 1.

Example 2 Preparation Method of the Chlorogenic Acid Crystal Form According to the Present Invention Processes: dissolving-filtering-freezing-filtering-collecting filter residue-freeze-drying
(1) Dissolving: Taking chlorogenic acid with purity more than 90%, adding purified water or water for injection to prepare solution of e chlorogenic acid with a concentration of 20 mg/ml-2 g/ml, and the dissolution temperature is 5° C.-70° C.;
(2) Filtering: The prepared aqueous solution of chlorogenic acid is filtered by a filter membrane or a filter element with an aperture size of 0.22 µm-200 µm, and the filtration temperature is 5° C.-70° C. The filtrate is collected;
(4) Freezing: The filtrate is frozen to 5° C.--20° C., at the ambient temperature of below 0° C.;
(5) Filtering: After freezing, the filtrate is filtered by a filter membrane with a aperture size of 0.22 µm-200 µm, and the filtration temperature is 0° C.-25° C. The filter residue is collected;
(6) Freeze-drying: The filtrate is placed in lyophilizer to freeze-dry, using a pre-freezing temperature of −10° C.--30° C., pre-freezing time of 1 h-5 h, a drying temperature of from −10° C.--30° C. to 30° C., a vacuum degree of 5 Pa-40 Pa, a warming time of 8 h-48 h, and drying for another 1 h-12 h at 30° C. After freeze-drying, the chlorogenic acid crystal form according to the present invention is obtained.

The crystal form prepared according to Example 2 is detected, and the relevant data are shown as follows.
Powder X-Ray Diffraction
Instrument model: Philips MRD X-ray diffractometer (Britain)
Detection criterion: Powder diffraction data issued by International Center for Diffraction Data (ICDD)
Testing conditions: target material Cu/graphite; tube voltage: 40 KV;
tube current: 30 mA; range 0.00-60.00 (Deg); scanning speed: 2 Deg/min
Testing results are shown in FIG. 2.

Figure 2:
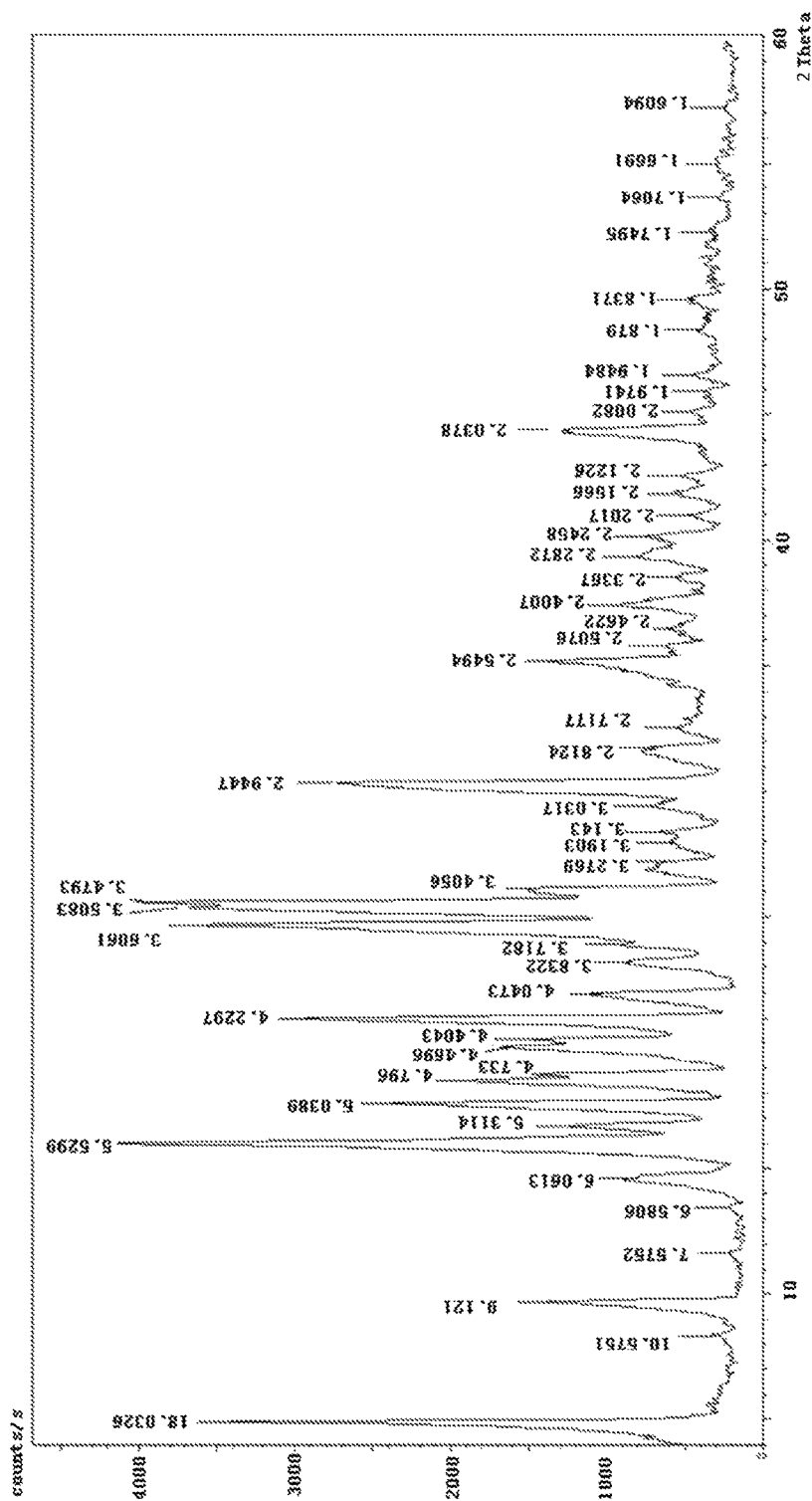
FIG. 2: X-ray powder diffraction spectrum of the chlorogenic acid crystal form prepared by Example 2

Comparison of FIG. 1 and FIG. 2 shows that the 2θ angle of the diffraction peaks in the powder X-ray diffraction pattern is almost same, confirming that the crystal forms obtained according to Examples 1 and 2 are identical.

Meanwhile, HPLC detection shows that the purity of chlorogenic acid is more than 98% in the crystal form obtained according to Example 2. Based on this purity result, after repeated analysis, the inventor found that as long as the purity of the sample reaches more than 90%, after filtering twice, the purity of chlorogenic acid in the product obtained after drying of the filter residue can be above 98%. This indicates that the impurity content can be effectively reduced after the freezing and re-filtering operations in Example 2, improving the purity of chlorogenic acid.

In addition, in the preparation method according to Method 2, the filter residue obtained after freezing and re-filtering operations is the intermediate of the crystal form obtained by freeze-drying. While filtering for the second time, a large amount of water is removed effectively by separating the filter residue from the filtrate. In later stage, the drying time of freeze-drying can be shorter than that of method 1, and the drying cost can be lower as well.

The advantageous effects of the present invention are illustrated by experiments as follows.

Experiment 1 Investigation on the Stability of Chlorogenic Acid Crystal Form According to the Present Invention
1. Long-Term Stability Test
Taking the chlorogenic acid crystal form prepared according to Example 1, packaged as the marketed, sampling and testing at the end of 3, 6, 9, 12, 18, 24, 36 and 48 months under the conditions that the temperature is 18±2° C. and the relative humidity is 60±10%, and carrying out crystal form examination by microscope at the end of 12, 24, 36 and 48 months. The results are shown as below.

TABLE 2

Experimental results of long-term stability (0-12 months)

| Time | Example | Appearance | Specific optical rotation ($[\alpha]_D^{20°}$) | Loss on drying (%) | Related substances (%) | | | | | In total (%) | Content (%) |
| | | | | | Caffeic acid | Other 1 | 2 | 3 | 4 | | |
| --- | --- | --- | --- | --- | --- | --- | --- | --- | --- | --- | --- |
| 0 month | Example 1 | almost white crystalline powder | −35.29 | 2.31 | 0.076 | 0.099 | 0.137 | 0.214 | 0.049 | 0.499 | 99.56 |
|  | Example 1 | almost white crystalline powder | −35.22 | 2.29 | 0.085 | 0.101 | 0.144 | 0.218 | 0.048 | 0.511 | 99.49 |
|  | Example 1 | almost white crystalline powder | −35.25 | 2.32 | 0.081 | 0.098 | 0.140 | 0.205 | 0.045 | 0.488 | 99.50 |
| 3 months | Example 1 | almost white crystalline powder | −35.20 | 2.30 | 0.089 | 0.102 | 0.142 | 0.230 | 0.049 | 0.523 | 99.47 |
|  | Example 1 | almost white crystalline powder | −35.22 | 2.31 | 0.097 | 0.105 | 0.151 | 0.237 | 0.050 | 0.543 | 99.41 |
|  | Example 1 | almost white crystalline powder | −35.20 | 2.29 | 0.093 | 0.103 | 0.148 | 0.228 | 0.046 | 0.525 | 99.43 |
| 6 months | Example 1 | almost white crystalline powder | −35.18 | 2.31 | 0.101 | 0.107 | 0.146 | 0.234 | 0.054 | 0.541 | 99.44 |
|  | Example 1 | almost white crystalline powder | −35.22 | 2.29 | 0.108 | 0.113 | 0.154 | 0.240 | 0.056 | 0.563 | 99.38 |
|  | Example 1 | almost white crystalline powder | −35.20 | 2.28 | 0.104 | 0.109 | 0.155 | 0.231 | 0.053 | 0.548 | 99.42 |
| 9 months | Example 1 | almost white crystalline powder | −35.18 | 2.32 | 0.108 | 0.116 | 0.162 | 0.255 | 0.058 | 0.591 | 99.38 |

TABLE 2-continued

Experimental results of long-term stability (0-12 months)

| Time | Example | Appearance | Specific optical rotation ($[\alpha]_D^{20°}$) | Loss on drying (%) | Related substances (%) Caffeic acid | 1 | 2 | 3 | 4 | In total (%) | Content (%) |
|---|---|---|---|---|---|---|---|---|---|---|---|
| | Example 1 | almost white crystalline powder | −35.22 | 2.31 | 0.116 | 0.122 | 0.167 | 0.261 | 0.061 | 0.611 | 99.30 |
| | Example 1 | almost white crystalline powder | −35.20 | 2.32 | 0.111 | 0.119 | 0.165 | 0.252 | 0.060 | 0.595 | 99.33 |
| 12 months | Example 1 | almost white crystalline powder | −35.20 | 2.28 | 0.115 | 0.121 | 0.163 | 0.260 | 0.062 | 0.606 | 99.32 |
| | Example 1 | almost white crystalline powder | −35.24 | 2.31 | 0.121 | 0.128 | 0.168 | 0.264 | 0.063 | 0.623 | 99.27 |
| | Example 1 | almost white crystalline powder | −35.18 | 2.29 | 0.118 | 0.130 | 0.169 | 0.265 | 0.063 | 0.627 | 99.23 |

TABLE 3

Experimental results of long-term stability (18-48 months)

| Time | Batch number | Appearance | Specific optical rotation ($[\alpha]_D^{20°}$) | Loss on drying (%) | Related substances (%) Caffeic acid | 1 | 2 | 3 | 4 | In total (%) | Content (%) |
|---|---|---|---|---|---|---|---|---|---|---|---|
| 18 months | Example 1 | almost white crystalline powder | −35.22 | 2.29 | 0.124 | 0.132 | 0.174 | 0.270 | 0.067 | 0.643 | 99.26 |
| | Example 1 | almost white crystalline powder | −35.20 | 2.28 | 0.133 | 0.136 | 0.174 | 0.272 | 0.065 | 0.647 | 99.24 |
| | Example 1 | almost white crystalline powder | −35.26 | 2.30 | 0.129 | 0.137 | 0.179 | 0.279 | 0.065 | 0.660 | 99.18 |
| 24 months | Example 1 | almost white crystalline powder | −35.20 | 2.32 | 0.130 | 0.140 | 0.178 | 0.278 | 0.070 | 0.666 | 99.17 |
| | Example 1 | almost white crystalline powder | −35.22 | 2.30 | 0.141 | 0.144 | 0.187 | 0.292 | 0.074 | 0.697 | 99.10 |
| | Example 1 | almost white crystalline powder | −35.20 | 2.31 | 0.136 | 0.142 | 0.185 | 0.286 | 0.072 | 0.685 | 99.14 |
| 36 months | Example 1 | almost white crystalline powder | −35.20 | 2.32 | 0.139 | 0.148 | 0.190 | 0.299 | 0.076 | 0.713 | 99.13 |
| | Example 1 | almost white crystalline powder | −35.24 | 2.31 | 0.150 | 0.150 | 0.194 | 0.301 | 0.074 | 0.719 | 99.05 |
| | Example 1 | almost white crystalline powder | −35.18 | 2.32 | 0.142 | 0.156 | 0.196 | 0.302 | 0.078 | 0.732 | 99.02 |
| 48 months | Example 1 | almost white crystalline powder | −35.20 | 2.34 | 0.149 | 0.156 | 0.219 | 0.303 | 0.092 | 0.770 | 98.85 |
| | Example 1 | almost white crystalline powder | −35.24 | 2.38 | 0.161 | 0.161 | 0.222 | 0.309 | 0.095 | 0.787 | 98.74 |
| | Example 1 | almost white crystalline powder | −35.18 | 2.36 | 0.153 | 0.157 | 0.218 | 0.306 | 0.091 | 0.772 | 98.80 |

Besides, the internal and external surface properties of the aluminum-plastic composite membrane were observed while sampling in 3, 6, 9, 12, 18, 24, 36 and 48 months, and the results indicated no obvious change. Crystal form examination by microscope was carried out at the end of 12, 24, 36 and 48 months, and as a result, it was single lamellar crystal at each time point.

It can be seen from the above data that the specific optical rotation of the chlorogenic acid crystal form according to the present invention basically did not change; loss on drying did not change obviously; the content of related substances gradually increased slightly, but at a modest extent; the content of chlorogenic acid gradually decreased slightly, but still remained above 98%. These results suggest that the chlorogenic acid crystal form of the present invention has good stability.

Experiment 2 Study on the Residual Solvent of Chlorogenic Acid Crystal Form According to the Present Invention An appropriate amount of acetonitrile was taken, accurately weighed, and N,N-dimethylformamide was added to prepare the internal standard solution containing 5 mg N,N-dimethylformamide per 1 ml; an appropriate amount of ethyl acetate was taken, weighed precisely, and N,N-dimethylformamide was added to prepare the solution containing 5 mg of ethyl acetate per 1 ml. 1 ml of the solution was accurately pipetted into a 10 ml volumetric flask, and 1 ml of the internal standard solution was precisely added, and diluted by adding N,N-dimethylformamide to the volume, and agitated to obtain the reference solution; 0.5 g of the chlorogenic acid crystal form prepared by Examples 1 and 2, and about 0.5 g of respective raw materials of each example, were taken and weighed precisely, then transferred to a 10 ml volumetric flask. 1 ml of the internal standard solution was added precisely, diluted with N,N-dimethylformamide to volume, and agitated, to obtain the testing solution. According to the gas chromatography method (the appendix V E of the second part of the Chinese Pharmacopoeia 2010), 30 m capillary column was used with 50% polyphenyl methylsiloxane as the stationary liquid, and its coating thickness was 1 μm. The column temperature was kept at 80° C. taking 1 μl of the reference solution and 1 μl of the testing solution were accurately taken, respectively, and injected into the gas chromatograph, to record the chromatogram. Calculating with the height ratio of peaks in accordance with internal standard method, the results are as follows:

TABLE 4

Experimental results of the residual solvent before and after preparation of samples

| Example | Residual solvent | |
|---|---|---|
| | Ethyl acetate (%) | Chinese Pharmacopoeia limit (%) |
| Raw material of Example 1 | 1.764 | 0.5 |
| Raw material of Example 2 | 2.314 | |
| Sample obtained in Example 1 | 0.254 | |
| Sample obtained in Example 2 | 0.252 | |

The data in Table 4 shows that the residual solvent can be effectively removed by the preparation means according to the present invention, and the residual solvent in the obtained sample are consistent with the standards of Chinese Pharmacopoeia.

The invention claimed is:

1. A crystalline form of chlorogenic acid having an orthorhombic crystalline structure of space group $P2_12_12_1$.

2. The crystalline form according to claim 1, having an X-ray powder diffraction pattern as shown in FIG. 1 or FIG. 2.

3. A process for preparing a crystalline form of chlorogenic acid of claim 1, comprising:
dissolving a crude chlorogenic acid with a purity of more than 90% and less than or equal to 98% in water to obtain a first solution;
filtering the first solution with a filter to obtain a first filtrate;
freezing the first filtrate to 5° C. to obtain a second solution;
filtering the second solution to get a filter residue; and
freeze-drying the filter residue to obtain the claimed crystal form of chlorogenic acid.

4. The process according to claim 3, wherein the crude chlorogenic acid is dissolved in water at 5° C. to 70° C.

5. The process according to claim 3, wherein a concentration of chlorogenic acid in the first solution is 20 mg/ml to 2 g/ml.

6. The process according to claim 5, wherein an aperture size of the filter used for filtration of the first solution, the second solution, or both is 0.22 μm to 200 μm.

7. The process according to claim 3, wherein the filter used for filtration of the first solution, the second solution, or both has a filter membrane or a filter element.

8. The process according to claim 3, wherein the filtering of the first solution is at 5° C. to 70° C. and the filtering of the second solution is at 0° C. to 25° C.

9. The process according to claim 3, wherein the freeze-drying of the filter residue comprises a pre-freezing step at a temperature of −10° C. to −30° C. for 1 h-5 h; a drying step that raises a temperature from a range between −10° C. and −30° C. to 30° C. in 8 h-48 h; and a further drying step at 30° C. for 1 h-12 h, wherein a pressure is 5 Pa to 40 Pa during freeze-drying.

10. A purification method of chlorogenic acid, comprising:
dissolving a crude chlorogenic acid with a purity of more than 90% and less than 98% in water to obtain a solution, filtering the solution to obtain a filtrate, freezing the filtrate to 5° C. to −20° C. to obtain a second solution, filtering the second solution to obtain a filter residue, freeze-drying the filter residue to obtain a chlorogenic acid with a purity of more than 98%.

11. The crystalline form according to claim 1 having unit cell parameters: a=7.7291(2) Å, b=10.9808(2) Å, c=36.5334 (7) Å, α=β=γ=90°, Z=8, and a unit cell volume of 3100.65 (11) Å$^3$.

12. A process for preparing a crystalline form of chlorogenic acid of claim 1, comprising: dissolving a crude chlorogenic acid having a purity of more than 98% in water to obtain a solution;
filtering the solution to obtain a filtrate; and
freeze-drying the filtrate.

13. The process according to claim 12, wherein a concentration of chlorogenic acid in the first solution is 10 mg/ml to 2 g/ml.

14. The process according to claim 12, wherein the filtering of the solution is at 5° C. to 70° C.

15. The process according to claim 12, wherein the freeze-drying of the filtrate comprises a pre-freezing step at a temperature of −20° C. to −50° C. for 1 hr to 8 hr; a warming step that raises a temperature from a range between −20° C. and −50° C. to 30° C. in 8 hr to 48 hr; and a drying step at 30° C. for 1 hr to 12 hr, wherein a pressure is 5 Pa to 40 Pa during freeze-drying.

16. The process according to claim 12, wherein an aperture size of the filter used for filtration of the solution is 0.22 μm-200 μm.

* * * * *